(12) United States Patent
Piestun et al.

(10) Patent No.: US 9,509,956 B2
(45) Date of Patent: Nov. 29, 2016

(54) HIGH-SPEED WAVEFRONT OPTIMIZATION

(71) Applicant: The Regents of the University of Colorado, a body corporate, Denver, CO (US)

(72) Inventors: Rafael Piestun, Boulder, CO (US); Donald Conkey, Boulder, CO (US)

(73) Assignee: The Regents Of The University Of Colorado, A Body Corporate, Denver, CO (US)

( * ) Notice: Subject to any disclaimer, the term of this patent is extended or adjusted under 35 U.S.C. 154(b) by 581 days.

(21) Appl. No.: 13/670,954

(22) Filed: Nov. 7, 2012

(65) Prior Publication Data

US 2013/0271592 A1  Oct. 17, 2013

Related U.S. Application Data

(60) Provisional application No. 61/556,617, filed on Nov. 7, 2011.

(51) Int. Cl.
*H04N 7/18* (2006.01)
*G02B 26/06* (2006.01)
*G01N 21/47* (2006.01)

(52) U.S. Cl.
CPC ............ *H04N 7/18* (2013.01); *G01N 21/4795* (2013.01); *G02B 26/06* (2013.01)

(58) Field of Classification Search
CPC .. G01N 21/47; G01N 21/4795; G02B 26/06; H04N 7/18
See application file for complete search history.

(56) References Cited

U.S. PATENT DOCUMENTS

| | | | | |
|---|---|---|---|---|
| 3,600,054 A * | 8/1971 | Gabor | | 359/25 |
| 3,717,843 A * | 2/1973 | Farrah et al. | | 367/8 |
| 3,756,683 A * | 9/1973 | Smith, Jr. | | 359/29 |
| 3,856,986 A * | 12/1974 | Macovski | | 348/40 |
| 4,037,918 A * | 7/1977 | Kato | | 359/29 |
| 4,480,892 A * | 11/1984 | Ishikawa | | 359/18 |
| 5,075,800 A * | 12/1991 | Hasman et al. | | 359/15 |
| 5,119,214 A * | 6/1992 | Nishii et al. | | 359/7 |
| 6,642,506 B1 * | 11/2003 | Nahum et al. | | 250/231.13 |
| 8,009,280 B1 * | 8/2011 | Erry | | G01J 9/00 351/205 |
| 2002/0051419 A1 * | 5/2002 | Itoh et al. | | 369/103 |
| 2004/0061917 A1 * | 4/2004 | Mushika et al. | | 359/223 |
| 2004/0095558 A1 * | 5/2004 | Whitehead et al. | | 353/30 |
| 2005/0063285 A1 * | 3/2005 | Mushika et al. | | 369/112.29 |
| 2005/0241203 A1 * | 11/2005 | Lizotte et al. | | 42/1.01 |
| 2006/0221419 A1 * | 10/2006 | Yoshikawa et al. | | 359/21 |
| 2008/0239421 A1 * | 10/2008 | Yoshikawa et al. | | 359/11 |

(Continued)

OTHER PUBLICATIONS

Berger et al., Reliability of associative recall based on data manipulations in phase encoded volume holographic storage systems, 2005, Institute of Physics Publishing—Journal of optics, Opt. 7, pp. 1-10.*

*Primary Examiner* — Peter D Le
(74) *Attorney, Agent, or Firm* — Maschoff Brennan (57) ABSTRACT

A wavefront is optimized imaging a sample. A binary off-axis hologram is encoded by selective adoption of states for each mirror of a deformable mirror device, which is illuminated with an incident beam of light. A single diffraction order that has encoded phase-mask information is selected from light reflected from the deformable mirror device and focused onto the sample. Light scattered from the sample is directed to a photodetector. A transmission matrix through the sample is calculated from light received by the photodetector.

23 Claims, 5 Drawing Sheets

(56) References Cited

U.S. PATENT DOCUMENTS

2009/0302122 A1* 12/2009 Begon ..................... G03H 1/02
  235/494
2010/0271922 A1* 10/2010 Iwamura et al. ............. 369/103

* cited by examiner

HIGH-SPEED WAVEFRONT OPTIMIZATION

CROSS-REFERENCE TO RELATED APPLICATION

This application is a nonprovisional of, and claims the benefit of the filing date of, U.S. Prov. Pat. Appl. No. 61/556,617, entitled "HIGH-SPEED WAVEFRONT OPTIMIZATION," filed Nov. 7, 2011 by Rafael Piestun and Donald Conkey, the entire disclosure of which is incorporated herein by reference.

STATEMENT REGARDING FEDERALLY SPONSORED RESEARCH OR DEVELOPMENT

This invention was made with government support under grant number DGE0801680 awarded by the National Science Foundation. The government has certain rights in the invention.

BACKGROUND OF THE INVENTION

This application relates to imaging. More specifically, this application relates to controlling light propagation through scattered media for imaging applications.

Certain imaging applications, such as biomedical imaging applications, require that light propagation through scattering media at high speeds be controlled. As light propagates through such media, and particularly through biological tissue, it becomes increasingly scattered, thus limiting the optical imaging depth to depths on the order of 1 mm. Wavefront control techniques have recently been introduced that allow for focusing through turbid media. These techniques rely on the deterministic nature of scattering processes to shape the incident wavefront to compensate for the scattered photons. Iterative methods divide the light incident on a scattering sample into N spatial input modes. The optimal phase of each mode is measured and set to create a focus on the opposing side of the scattering material. Other iterative techniques optimize the input modes in parallel, thus increasing the speed at which the focus is formed.

Another technique measures the transmission matrix through the scattering material. With the transmission matrix, the relationship between the input modes and output modes through the sample is understood quantitatively and phase masks can be calculated that focus to any mode in the output plane. Other techniques apply a phase conjugation to a recorded scattered field for focusing through turbid media.

Techniques that rely on the deterministic nature of multiple scattering to shape the incident wavefront and to pre-compensate for the scattering effects of light propagation encounter difficulties in certain media, notably in living biological materials. The imaging depth into biological materials is limited by scattering, and living biological materials have speckle decorrelation times on the millisecond timescale. This fast rate of change limits the value of various methods of focusing through turbid media, making them too slow because of measurement-rate limitations from the wavefront modulation device. Such methods typically use liquid-crystal spatial light modulators ("LC-SLM") for phase-only wavefront modulation, which is more efficient for creating a focus than amplitude-only modulation. the LC-SLMs' switching speed is limited by the rate at which the liquid crystals can align in the device, typically on the order of 10s of Hz and much slower than the kHz rate needed for the millisecond timescale of biological tissue.

There is accordingly a need in the art for improved methods and systems for wavefront optimization.

SUMMARY

Embodiments of the invention provide methods and systems for optimizing a wavefront for imaging a sample. A binary off-axis hologram is encoded by selective adoption of one of a plurality of states for each of a plurality of mirrors comprised by a deformable mirror device. The deformable mirror device is illuminated with an incident beam of light. A single diffraction order is selected from light reflected from the deformable mirror device. The single diffraction order comprises encoded phase-mask information. The selected diffraction order is focused onto the sample. Light scattered from the sample is directed to a photodetector. A transmission matrix through the sample is calculated from light received by the photodetector.

In some embodiments, the single diffraction order is the −1 diffraction order. The binary off-axis hologram may comprise a binary Lee hologram. The incident beam of light may be substantially monochromatic and/or substantially collimated.

A plane behind the sample may be imaged onto a pinhole placed before the photodetector. In some instances, a size of the pinhole may match a speckle size of the light scattered from the sample. A secondary image plane may also be created at the surface of an imager. Calculation of the transmission matrix may comprise applying a three-phase method by interfering each of a plurality of Hadamard basis elements with phase references of 0, $\pi/2$, and $\pi$.

BRIEF DESCRIPTION OF THE DRAWINGS

A further understanding of the nature and advantages of the present invention may be realized by reference to the remaining portions of the specification and the drawings, wherein like reference labels are used through the several drawings to refer to similar components. In some instances, reference labels are followed with a hyphenated sublabel; reference to only the primary portion of the label is intended to refer collectively to all reference labels that have the same primary label but different sublabels.

DETAILED DESCRIPTION OF EXEMPLARY EMBODIMENTS

Embodiments of the invention provide a high-speed phase-mask wavefront optimization technique that uses off-axis binary amplitude holography with a deformable mirror device. The introduction of off-axis holography implements phase-only modulation of the wavefront using the high switching speed of deformable mirror devices. Embodiments of the invention thus minimize the effects of unwanted cross-correlation terms from a deformable-mirror-device array. Phase-only wavefront modulation has an ideal theoretical enhancement of five times binary amplitude modulation for the same number of input nodes. Considering that biological samples have a limited timeframe for focusing in the tens of milliseconds, frame-rate limitations of particular deformable mirror devices limit the possible number of optimized modes usable under such conditions. Accordingly, embodiments of the invention combine an array of binary pixels into fewer modes but implementing phase modulation. Merely by way of example, in some embodiments, the deformable mirror devices have a maximum full-image frame rate of 22.7 kHz and a 1024×768 binary pixel array is used.

Using holography with the binary amplitude modulating deformable mirror device allows for the creation of phase-only variations. Binary amplitude off-axis holography is suitable for the generation of uniform-amplitude phase-modulated images, enabling the modulation of incident phase at the high speeds made possible by the deformable mirror device. In certain embodiments, amplitude holograms are generated using the Lee method as described in M. Cui, E. J. McDowell, and C. Yang, "An in vivo study of turbidity suppression by optical phase conjugation (TSOPC) on rabbit ear," Opt. Express 18, 25-30 (2009), the entire disclosure of which is incorporated herein by reference for all purposes. This technique uses an off-axis reference wave to encode the desired phase distribution $\phi(x,y)$. For instance, the amplitude hologram $t(x,y)$ may be defined by carrier frequency $\alpha$:

$$t(x,y)=0.5[1+\cos(2\pi(x-y)\alpha-\phi(x,y))].$$

In this implementation, the hologram is put off-axis diagonally, but other implementations are possible in different embodiments. The carrier frequency $\alpha$ is selected to minimize crosstalk by providing a sufficiently large separation of the −1 order from the 0 order beam. The binary amplitude hologram $h(x,y)$ is generated by thresholding the amplitude hologram $t(x,y)$. In order to maximize the diffraction efficiency, the width of fringes used may be half the fringe periodicity:

$$h(x, y) = \begin{cases} 1; t(x, y) > 0.5 \\ 0; \text{otherwise} \end{cases}.$$

The desired wavefront is produced in the −1 diffraction order. To create the image, an aperture placed in the Fourier plane of the hologram around the −1 diffraction order blocks out all other diffraction orders. Then after another Fourier transforming lens, the image is created with substantially uniform intensity and phase variation $\phi(x,y)$. Use of a binary hologram in this way is merely exemplary; many other encoding techniques (either iterative or deterministic) may be used in alternative embodiments, and both amplitude and phase may be encoded simultaneously.

Figure 1A:
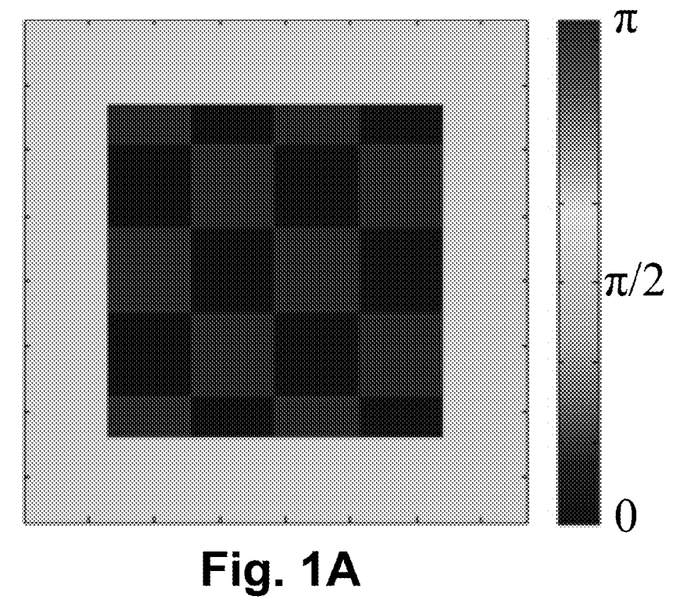
FIG. 1A provides an example of a desired phase distribution for a single Hadamard basis element and FIG. 1B shows the binary-amplitude Lee hologram that encodes the phase distribution shown in FIG. 1A.
Figure 1B:
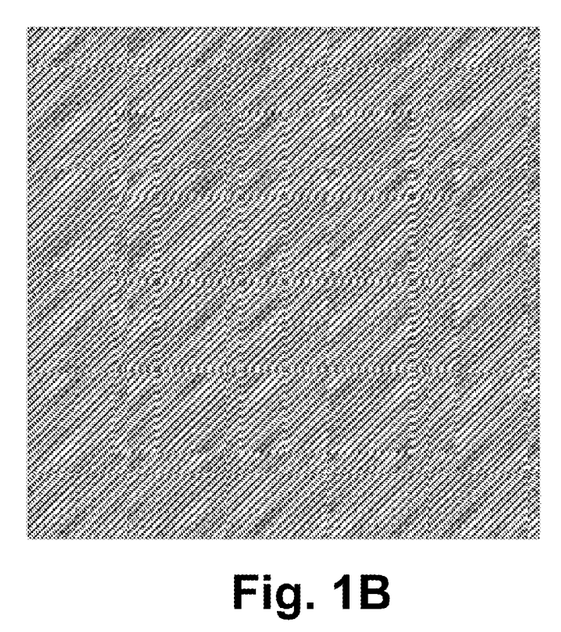

To illustrate, FIG. 1A provides an example of a desired phase distribution for a single Hadamard basis element. The basis element is surrounded by the reference part of the beam for transmission-matrix measurement. FIG. 1B correspondingly shows the binary amplitude Lee hologram that encodes the phase distribution shown in FIG. 1A.

Figure 2:
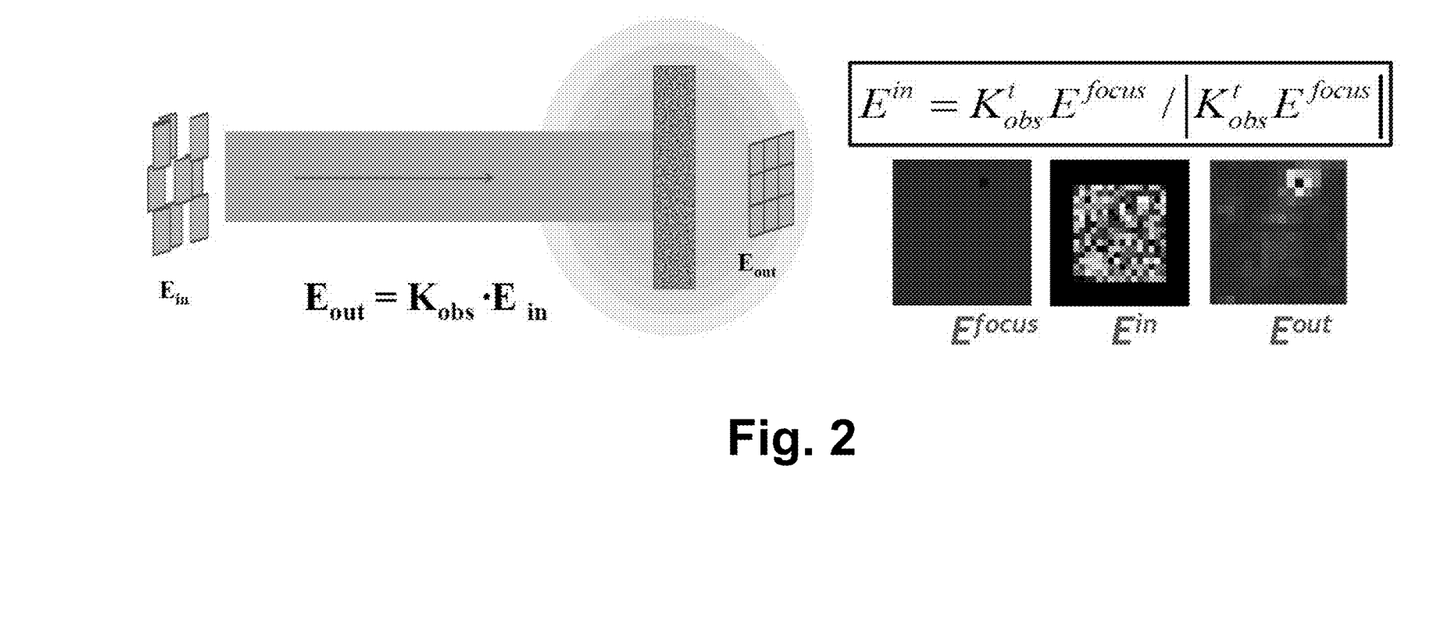
FIG. 2 provides a schematic illustration of principles for wavefront optimization used in embodiments of the invention.

Wavefront determination may be accomplished using a variety of techniques, as understood by those of skill in the art. Illustrated herein is a transmission-matrix focusing method that advantageously uses a set of predefined phase masks and requires a minimal number of measurements. Using a predefined set of phase masks minimizes data-transfer time between the deformable mirror device and computer, thereby allowing the deformable mirror device to display all preloaded images at a maximum frame rate. The observed transmission matrix $K_{obs}$ is measured by calculating the complex field response for a set of given input basis modes. In one embodiment, the Hadamard basis set is selected because it can be represented as a phase basis with uniform amplitude. The complex field response is measured by interference between the Hadamard basis element and known phase reference beams. The procedure is illustrated schematically in FIG. 2, in which an input field $E_{in}$ is acted on by transmission matrix $K_{obs}$ to generate output field $E_{out}$ $=K_{obs}E_{in}$. The input field $E_{in}$ can accordingly be determined from a focus field $E_{focus}$ as $$E_{in} = \frac{K^\dagger_{obs}E_{focus}}{|K^\dagger_{obs}E_{focus}|},$$

where the superscript dagger denotes the conjugate transpose.

To limit the number of measurements made, one embodiment uses a three-phase method to recover the complex field, although a four-phase method may alternatively be used in other embodiments. This technique interferes each Hadamard basis element with phase references of 0, $\pi/2$, and $\pi$. Furthermore, because of speed limitations on charge-coupled devices, embodiments may use a photodetector for high-speed intensity measurements. This simplifies the transmission matrix measured into an N×1 matrix, defined as the response at a single output mode to N input modes. The transmission-matrix response for Hadamard basis element n is calculated with the intensity measurements at the output mode for all three phase references:

$$E_{in} = \frac{K^\dagger_{obs}}{|K^\dagger_{obs}|}.$$

With the transmission matrix measured, the appropriate phase mask for creating a focus at the single output mode is calculated as $$k^n_{obs} = \frac{1}{3}(I^\pi - I^{\pi/2}) + \frac{i}{3}(I^0 - I^{\pi/2}).$$

The three phase references transmission-matrix measurement method can find a suitable phase mask after measurements of 3N predefined phase masks, providing a 25% improvement in speed over 4N measurements. Simulations demonstrate that with experimental-level noise, the overall signal-to-background enhancement is comparable for the three- and four-phase methods.

Figure 3:
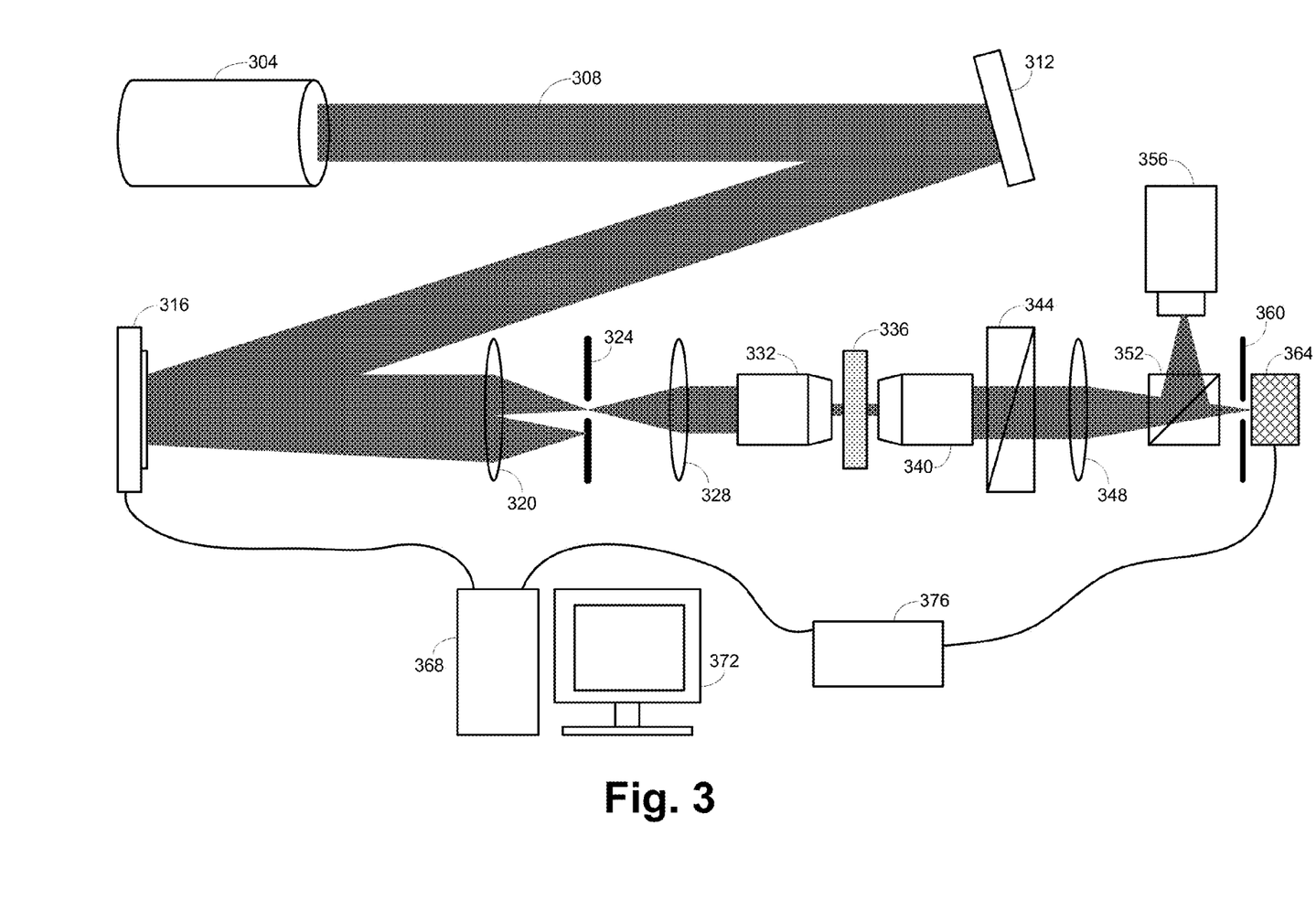
FIG. 3 is a diagram illustrating a system used for wavefront optimization according to embodiments of the invention.

An overview of a system for wavefront optimization used in embodiments of the invention is illustrated with FIG. 3, in which a light source 304 generates a light beam 308 that illuminates the deformable mirror device 316, perhaps after encountering a folding mirror 312. The light beam 308 may be collimated as illustrated in the drawing, such as may be achieved by using a laser light source 304. In one embodiment, the light source 304 comprises a 532-nm laser, although other wavelengths may be used in different embodiments. Furthermore, other types of light sources may be used in alternative embodiments, perhaps with optical elements disposed to achieve the desired collimation. In the illustrative embodiment the deformable mirror device comprises an array of 1024×768 mirrors, such as supplied by the DLP Discovery Kit D4100, which has been used by the inventors in implementations of the invention.

Each mirror is individually controlled to two angular positions, which may be used to encode the binary amplitude Lee hologram. For purposes of illustration, N=256 inputs is chosen to correspond to a single output mode in the form of a photodetector 364. In an illustration of this embodiment, the transmission-matrix measurement method was implemented with the deformable mirror device 316 to generate 768 binary amplitude holograms. These consist of 256 Hadamard basis elements with three reference phases per element, as illustrated with the exemplary phase distribution of FIG. 1A, with the centered Hadamard basis element surrounded by the reference. All 768 holograms are loaded onto the deformable-mirror-device memory. With the holograms in the deformable-mirror-device memory and with high-speed software, the deformable memory device may be controlled at its maximum frame rate.

Optically following the deformable mirror device 316 is a Fourier transforming lens 320. An iris 324 placed after this lens in the Fourier plane blocks all diffraction orders except for the −1 order, where the phase-mask information is encoded. The −1 order light is then propagated through a second Fourier transforming lens 328, which images the phase mask at the back aperture of an objective lens 332 that focuses the beam on the scattering sample 336. In an illustrative embodiment, the objective lens 332 comprises a 20×(numerical aperture of 0.50) lens. A second objective lens 340 images a plane behind the scattering sample onto a pinhole 360 placed before the photodetector 364. In the illustrative embodiment, the second objective lens 340 comprises a 100×(numerical aperture of 0.75) lens and the pinhole 360 comprises a 50-μm pinhole. More generally, the back objective and the pinhole size are selected to match the pinhole to the speckle size of scattered light from the sample. Relaying the image to the pinhole 360 may comprise transmission through a polarizer 344 and focusing lens 348, and perhaps also a beamsplitter 352 to create a secondary image plane at the surface of a charge-coupled device to image the focus spot.

The photodetector voltage is digitized may be transmitted to a computational device 368, shown in the drawing as comprising a computer with a monitor 372, through an oscilloscope 376. The computational device calculates the transmission matrix through the scattering material to the single output mode. By using a photodetector, the intensity measurement is oversampled in time and an average value may be used for the intensity measure. When using the three-phase method described above, three masks are provided for each Hadamard basis element, each providing a reference beam for interference to determine the complex field at the output plane.

The off-axis binary amplitude hologram focusing system and method has been tested experimentally by the inventors using 120-grit ground glass (Edmund Optics, NT83-381) as the scattering medium. Each binary amplitude hologram was displayed on the deformable mirror device for 44 μs, i.e. at a rate of 22.7 kHz. This frame rate was limited by the mirror switching time of 22 μs. Thus, all 768 measurements for transmission matrix determination occurred in 33.8 ms. The photodetector signal was digitized and sent to the computer where the average intensity value for each measurement was used to calculate the transmission matrix of the system. Using the transmission matrix of the 256 input modes mapped to the single output mode, the phase-conjugate mask was calculated and used to maximize the intensity of the light at the photodetector. The enhancement of the focus was calculated using the focus image taken with the charge-coupled device. Using this system, the inventors have demonstrated signal enhancements of 160±4 over the background intensity level, which is comparable to enhancements obtained using a phase-only liquid-crystal spatial light modulator.

Figure 4A:
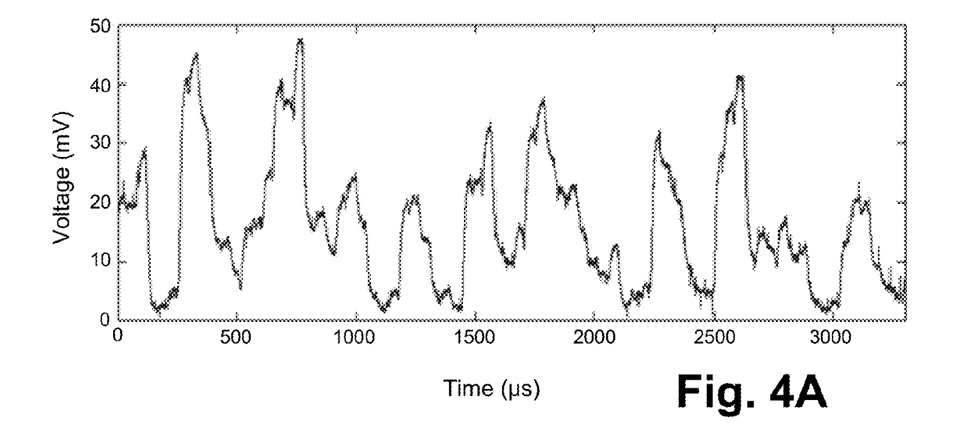
FIG. 4A shows digitized sampling data from the photodetector of FIG. 3 through diffuse glass, showing the intensity of the first 25 Hadamard basis modes interfered with three phase references.
Figure 4B:
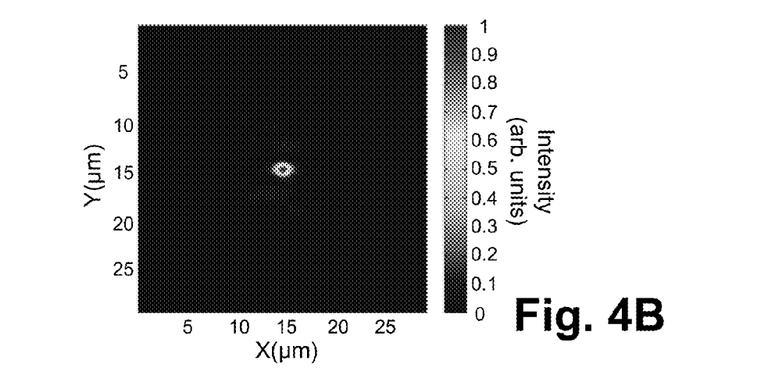
FIG. 4B shows a focus spot corresponding to the data of FIG. 4A with enhancement of 450 after optimization with 1024 modes.
Figure 4C:
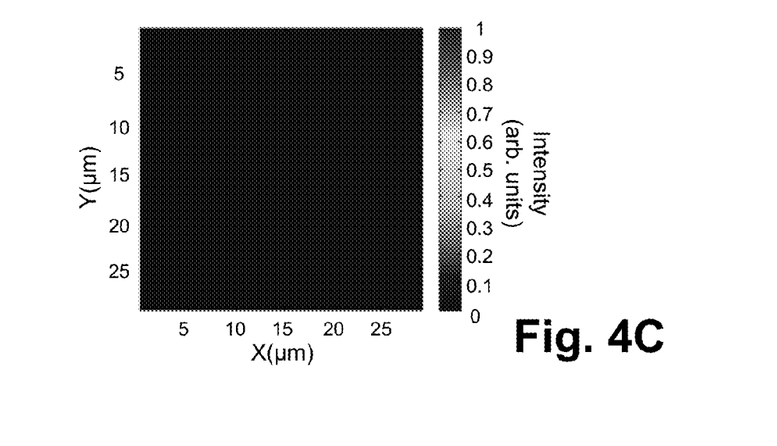
FIG. 4C shows a speckle field corresponding to the data of FIG. 4A without the optimized phase mask.

FIG. 4A illustrates how the intensity of the output mode varies with each binary amplitude hologram. These sample data correspond to the first 25 Hadamard basis elements and their three phase references, and were used to calculate the transmission matrix. The inventors have also implemented the transmission matrix with 1024 input modes and have measured enhancements of 447±7. FIG. 4B shows an example of a focus spot created through the scattering sample with 1024 modes, with signal enhancement of 450 over the background level, while FIG. 4C shows the intensity distribution with a single Hadamard basis element and reference phase hologram on the deformable mirror device to illustrate the unoptimized speckle field. With either 256 or 1024 input modes, a focus spot with FWHM of 1.0 μm was created.

Figure 5A:
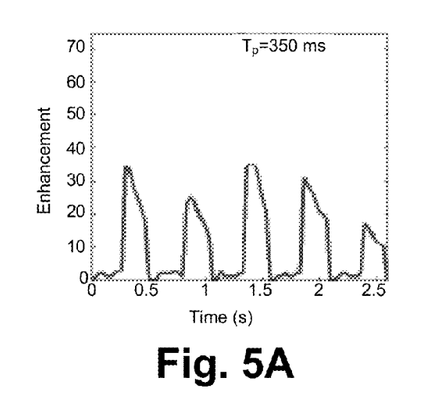
FIGS. 5A, 5B, and 5C show system focus enhancement versus time with dynamic turbid samples of decorrelation times of 350 ms, 650 ms, and 850 ms respectively.
Figure 5B:
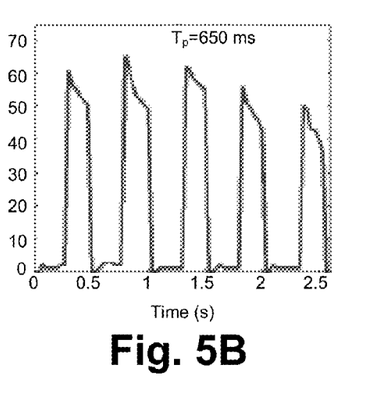
Figure 5C:
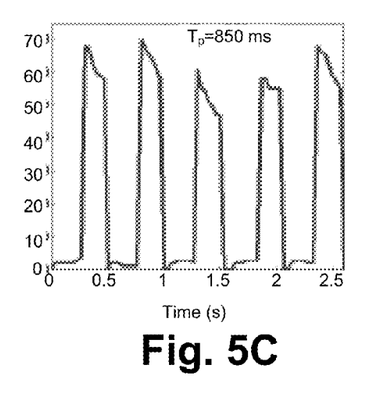
Figure 5D:
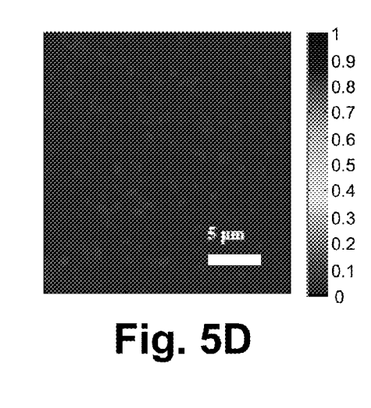
FIG. 5D shows the speckle field corresponding to the data of FIGS. 5A-5C before optimization.
Figure 5E:
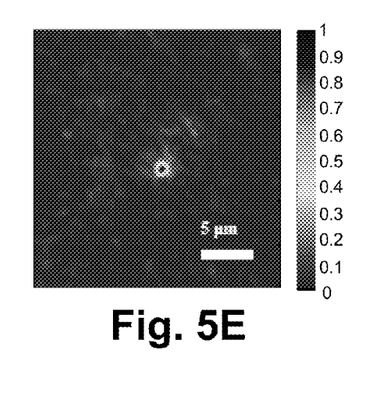
FIG. 5E shows the focal spot corresponding to the data of FIGS. 5A-5C after optimization.
Figure 5F:
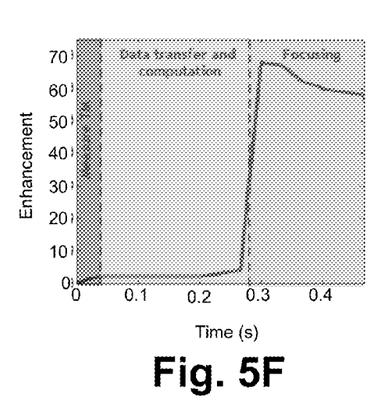
FIG. 5F summarizes system timing for transmission-matrix measurement, data transfer and computation, and focusing.

FIGS. 5A-5C show system enhancement versus time with dynamic turbid samples of different decorrelation time, namely 350 ms for FIG. 5A, 650 ms for FIG. 5B, and 850 ms for FIG. 5C. The speckle field before optimization is shown in FIG. 5D and the focal spot after optimization is shown in FIG. 5E. A summary of system timing is provided in FIG. 5E, with measurement of the transmission matrix taking 34 ms in the first portion of the drawing, data transfer and computation taking 270 ms in the second portion of the drawing, and displaying the optimized mask taking 200 ms in the third portion of the drawing.

These results thus demonstrate high-speed wavefront optimization for focusing through turbid media using a deformable mirror device with off-axis binary amplitude holography to encode the Hadamard phase basis and references. Measurement of the transmission matrix using a three-phase method improves the total measurement time by about 25%. with this improvement and phase-algorithm implementation with a high-speed deformable mirror device for hologram encoding, an order of magnitude improvement in measurement speed is realized over other wavefront determination methods, notable a three-order-of-magnitude improvement over LC-SLM methods.

The off-axis binary amplitude technique described herein finds utility in systems for imaging or detection in biological materials. By measuring seven basis modes per millisecond, this method may have sufficient speed to overcome the fast speckle decorrelation times of biological samples and generate sufficient focusing to be useful for a variety of biomedical sensing and imaging applications.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed:

1. A method of optimizing a wave front for imaging a sample, the method comprising:
    encoding a binary off-axis hologram by selective adoption of one of a plurality of states for each of a plurality of mirrors comprised by a deformable mirror device;
    illuminating the deformable mirror device with an incident beam of light;
    selecting a single diffraction order from light reflected from the deformable mirror device, wherein the single diffraction order comprises encoded phase-mask information;
    focusing the selected single diffraction order onto the sample;
    directing light scattered from the sample to a photodetector;
    digitizing voltage readings representing light intensity at the photodetector from the light scattered from the sample;
    calculating a transmission matrix through the sample from the digitized voltage readings;
    calculating a phase-conjugate mask from the transmission matrix; and
    increasing at least a portion of the voltage readings representing light intensity at the photodetector using the calculated phase-conjugate mask.

2. The method recited in claim 1 wherein the single diffraction order is the −1 diffraction order.

3. The method recited in claim 1 wherein the binary off-axis hologram comprises a binary Lee hologram.

4. The method recited in claim 1 wherein the incident beam of light is substantially monochromatic.

5. The method recited in claim 1 wherein the incident beam of light is substantially collimated.

6. The method recited in claim 1 wherein directing the light scattered from the sample to a photodetector comprises imaging a plane behind the sample onto a pinhole placed before the photodetector.

7. The method recited in claim 6 wherein a size of the pinhole matches a speckle size of the light scattered from the sample.

8. The method recited in claim 1 further comprising creating a secondary image plane with the light scattered from the sample at a surface of an imager.

9. The method recited in claim 1 wherein calculating the transmission matrix comprises applying a three-phase method by interfering each of a plurality of Hadamard basis elements with phase references of 0, $\pi/2$, and $\pi$.

10. A system for optimizing a wavefront for imaging a sample, the system comprising:
    a deformable mirror device having a plurality of mirrors, each such mirror adopting one of a plurality of states to encode a binary off-axis hologram;
    a light source disposed to illuminate the deformable mirror device with an incident beam of light;
    an optical element disposed to select a single diffraction order from light reflected from the deformable mirror device, wherein the single diffraction order comprises encoded phase-mask information;
    a lens disposed to focus the selected single diffraction order onto the sample;
    a photodetector configured to digitize voltage values representing the intensity of light incident on the photodetector;
    an optical train disposed to direct light scattered from the sample to the photodetector; and
    a computational unit in communication with the photodetector and having instructions to calculate a transmission matrix of the system through the sample from the digitized voltage values received from the photodetector, having instructions to calculate a phase-conjugate mask from the transmission matrix, and having instructions to calculate an increase in the digitized voltage values representing light intensity at the photodetector using the calculated phase-conjugate mask.

11. The system recited in claim 10 wherein the single diffraction order is the −1 diffraction order.

12. The system recited in claim 10 wherein the binary off-axis hologram comprises a binary Lee hologram.

13. The system recited in claim 10 wherein the incident beam of light is substantially monochromatic.

14. The system recited in claim 10 wherein the incident beam of light is substantially collimated.

15. The system recited in claim 10 wherein the optical element comprises a Fourier transforming lens.

16. The system recited in claim 10 wherein the optical train is configured to image a plane behind the sample onto a pinhole placed before the photodetector.

17. The system recited in claim 16 wherein a size of the pinhole matches a speckle size of the light scattered from the sample.

18. The system recited in claim 10 wherein the optical train is configured to create a secondary image plane with the light scattered from the sample at a surface of an imager.

19. The system recited in claim 10 wherein the instructions to calculate the transmission matrix comprise instruction to apply a three-phase method by interfering each of a plurality of Hadamard basis elements with phase references of 0, $\pi/2$, and $\pi$.

20. A system comprising:
    a light source that produces a wavefront;
    a deformable mirror that modulates the wavefront produced by the light source;
    an optical system disposed to focus light reflected from the deformable mirror onto a sample through a scattering medium;
    a light sensing element disposed to digitize voltage values representing the intensity of light incident on the light sensing element; and
    a computational unit in communication with the light sensing element and having instructions to calculate a transmission matrix of the system through the sample from light received by the light sensing element, having instructions to calculate a phase-conjugate mask from the transmission matrix, and having instructions to increase at least a portion of the digitized voltage values representing light intensity at the light sensing element using the calculated phase-conjugate mask.

21. The system according to claim 20, wherein the deformable mirror produces a plurality of binary amplitude holograms.

22. The system according to claim 20, wherein the light sensing element comprises a photodetector.

23. The system according to claim 20, wherein the deformable mirror modulates the light source producing a wavefront with phase-only modulation.

* * * * *